United States Patent
Chudzik et al.

(10) Patent No.: US 9,456,806 B2
(45) Date of Patent: Oct. 4, 2016

(54) BIOPSY PROBE MECHANISM HAVING MULTIPLE ECHOGENIC FEATURES

(71) Applicant: C. R. Bard, Inc., Tempe, AZ (US)

(72) Inventors: Rafal Chudzik, Peoria, AZ (US); Jason G. Seiger, Gilbert, AZ (US); Jennifer Smith, Mesa, AZ (US); Charles Simpson, Westlake Village, CA (US)

(73) Assignee: C.R. Bard, Inc., Murray Hill, NJ (US)

( * ) Notice: Subject to any disclaimer, the term of this patent is extended or adjusted under 35 U.S.C. 154(b) by 364 days.

(21) Appl. No.: 13/929,314

(22) Filed: Jun. 27, 2013

(65) Prior Publication Data

US 2013/0289442 A1 Oct. 31, 2013

Related U.S. Application Data

(63) Continuation of application No. 12/645,567, filed on Dec. 23, 2009, now Pat. No. 8,480,592.

(51) Int. Cl.
| | |
|---|---|
| *A61B 10/02* | (2006.01) |
| *A61B 19/00* | (2006.01) |
| *A61M 25/01* | (2006.01) |
| *A61B 10/00* | (2006.01) |

(52) U.S. Cl.
CPC ....... *A61B 10/0233* (2013.01); *A61B 10/0275* (2013.01); *A61B 10/0283* (2013.01); *A61B 19/54* (2013.01); *A61B 2010/0093* (2013.01); *A61B 2010/0208* (2013.01); *A61B 2019/462* (2013.01); *A61B 2019/4857* (2013.01); *A61B 2019/5425* (2013.01); *A61M 25/0108* (2013.01)

(58) Field of Classification Search
CPC .......... A61B 10/0233; A61B 10/0266; A61B 10/0275; A61B 19/54; A61B 2019/462; A61B 2019/4857; A61B 2019/5425; A61M 25/0108

See application file for complete search history.

(56) References Cited

U.S. PATENT DOCUMENTS

| | | |
|---|---|---|
| 3,844,272 A | 10/1974 | Banko |
| 4,401,124 A | 8/1983 | Guess et al. |
| 4,869,259 A * | 9/1989 | Elkins ............... A61B 8/0833 600/458 |
| RE33,258 E | 7/1990 | Onik et al. |
| 4,977,897 A | 12/1990 | Hurwitz |
| 5,048,530 A | 9/1991 | Hurwitz |
| 5,081,997 A | 1/1992 | Bosley, Jr. et al. |
| 5,161,542 A | 11/1992 | Palestrant |

(Continued)

FOREIGN PATENT DOCUMENTS

| | | |
|---|---|---|
| EP | 2016907 A2 | 1/2009 |
| GB | 2018601 A | 10/1979 |

(Continued)

*Primary Examiner* — Devin Henson

(57) ABSTRACT

A biopsy probe mechanism includes an elongate sample receiving member having a longitudinal axis and having a sample receiving notch. The elongate sample receiving member and a cutting cannula are movable relative to one another along a longitudinal axis. A first echogenic feature is established on the elongate sample receiving member and a second echogenic feature is established on the cutting cannula. The elongate sample receiving member and the cutting cannula are configured to have a first position in which the first echogenic feature is in longitudinal alignment with the second echogenic feature, and configured such that when the elongate sample receiving member and the cutting cannula are moved relative to one another from the first position, the first echogenic feature and the second echogenic feature are out of longitudinal alignment.

10 Claims, 3 Drawing Sheets

(56) References Cited

U.S. PATENT DOCUMENTS

| | | |
|---|---|---|
| 5,201,314 A | 4/1993 | Bosley et al. |
| 5,259,837 A | 11/1993 | Van Wormer |
| 5,335,671 A | 8/1994 | Clement |
| 5,383,466 A | 1/1995 | Partika |
| 5,474,075 A | 12/1995 | Goldberg et al. |
| 5,490,521 A | 2/1996 | Davis et al. |
| 5,526,822 A | 6/1996 | Burbank et al. |
| 5,601,585 A | 2/1997 | Banik et al. |
| 5,769,086 A | 6/1998 | Ritchart et al. |
| 5,820,554 A | 10/1998 | Davis et al. |
| 5,830,219 A | 11/1998 | Bird et al. |
| 5,921,933 A | 7/1999 | Sarkis et al. |
| 5,928,164 A | 7/1999 | Burbank et al. |
| 5,967,988 A | 10/1999 | Briscoe et al. |
| 6,018,676 A | 1/2000 | Davis et al. |
| 6,086,544 A | 7/2000 | Hibner et al. |
| 6,106,473 A | 8/2000 | Violante et al. |
| 6,120,462 A | 9/2000 | Hibner et al. |
| 6,273,862 B1 | 8/2001 | Privitera et al. |
| 6,331,166 B1 | 12/2001 | Burbank et al. |
| 6,428,487 B1 | 8/2002 | Burdorff et al. |
| 6,585,664 B2 | 7/2003 | Burdorff et al. |
| 6,610,016 B1 | 8/2003 | Violante et al. |
| 6,659,105 B2 | 12/2003 | Burbank et al. |
| 6,723,052 B2 | 4/2004 | Mills |
| 6,752,768 B2 | 6/2004 | Burdorff et al. |
| 6,860,856 B2 | 3/2005 | Ward et al. |
| 7,014,610 B2 | 3/2006 | Koulik |
| 7,153,274 B2 | 12/2006 | Stephens et al. |
| 7,189,206 B2 | 3/2007 | Quick et al. |
| 7,226,424 B2 | 6/2007 | Ritchart et al. |
| 7,347,829 B2 | 3/2008 | Mark et al. |
| 7,648,466 B2 | 1/2010 | Stephens et al. |
| 7,693,567 B2 | 4/2010 | Tsonton et al. |
| 2003/0009100 A1 | 1/2003 | Derendorf et al. |
| 2005/0043756 A1 | 2/2005 | Lavelle et al. |
| 2006/0247530 A1 | 11/2006 | Hardin, Jr. et al. |
| 2006/0271082 A1* | 11/2006 | Kirchhevel ...... A61B 17/32002 606/170 |
| 2008/0097213 A1 | 4/2008 | Carlson et al. |
| 2008/0154151 A1 | 6/2008 | Ritchart et al. |
| 2011/0152715 A1 | 6/2011 | Delap et al. |
| 2011/0160592 A1 | 6/2011 | Mitchell |
| 2011/0190660 A1* | 8/2011 | Levy .............................. 600/566 |
| 2012/0220894 A1* | 8/2012 | Melsheimer .................. 600/567 |

FOREIGN PATENT DOCUMENTS

| | | |
|---|---|---|
| WO | 2005072621 A1 | 8/2005 |
| WO | 2008062451 A2 | 5/2008 |
| WO | 2009137288 A2 | 11/2009 |

* cited by examiner

BIOPSY PROBE MECHANISM HAVING MULTIPLE ECHOGENIC FEATURES

CROSS-REFERENCE TO RELATED APPLICATIONS

This is a continuation of U.S. patent application Ser. No. 12/645,567, entitled "BIOPSY PROBE MECHANISM HAVING MULTIPLE ECHOGENIC FEATURES", filed Dec. 23, 2009, now U.S. Pat. No. 8,480,592.

MICROFICHE APPENDIX

None.

GOVERNMENT RIGHTS IN PATENT

None.

BACKGROUND OF THE INVENTION

1. Field of the Invention

The present invention relates to a medical device, and, more particularly, to a biopsy probe mechanism having multiple echogenic features.

2. Description of the Related Art

A biopsy may be performed on a patient to help in determining whether the cells in a tissue lesion to be biopsied are cancerous. A typical biopsy apparatus includes a hand-held driver assembly having one or more drivers that drivably engage driven components of a disposable biopsy probe mechanism configured for releasable attachment to the driver assembly. The biopsy probe mechanism typically includes a biopsy cannula, e.g., a needle, having a sample port for receiving the tissue to be sampled, and a cutting cannula for severing tissue received in the sample port.

In the prior art, it is known to provide a surgical instrument, such as a needle, with a roughened surface portion for use with an ultrasound imagining system to provide real-time monitoring of the location of a specific portion of the needle during insertion and guidance inside the patient's body.

SUMMARY OF THE INVENTION

The present invention provides a biopsy probe mechanism having a plurality of echogenic features to enhance visualization of the relative movement of biopsy probe components when using ultrasound imaging.

The invention, in one form thereof, is directed to a biopsy probe mechanism. The biopsy probe mechanism includes an elongate sample receiving member having a longitudinal axis and having a sample receiving notch. A cutting cannula is arranged coaxially with the sample receiving member. The elongate sample receiving member and the cutting cannula are movable relative to one another along the longitudinal axis between a first relative position and a second relative position. A plurality of echogenic features includes a first echogenic feature and a second echogenic feature. The first echogenic feature is established on the elongate sample receiving member and the second echogenic feature is established on the cutting cannula. The first echogenic feature is in longitudinal alignment with the second echogenic feature when the elongate sample receiving member and the cutting cannula are in the first relative position. The first echogenic feature is out of longitudinal alignment with the second echogenic feature when the elongate sample receiving member and the cutting cannula are in the second relative position.

The invention, in another form thereof, is directed to a biopsy probe mechanism for use in ultrasonic imaging. The biopsy probe mechanism includes an elongate sample receiving member having a longitudinal axis and having a sample receiving notch. A cutting cannula is arranged coaxially with the sample receiving member. The elongate sample receiving member and the cutting cannula are movable relative to one another along the longitudinal axis between a first relative position, wherein the sample receiving notch is closed by the cutting cannula, and a second relative position wherein the sample receiving notch is open. A plurality of echogenic features includes a first set of longitudinally spaced echogenic features established on the sample receiving member, with the sample receiving notch being located between two longitudinally spaced echogenic features of the first set of echogenic features.

The invention, in another form thereof, is directed to a biopsy apparatus for use in conjunction with an ultrasound device. The biopsy device includes a driver assembly and a biopsy probe mechanism coupled to the driver assembly. The driver assembly is configured to provide operative control over the biopsy probe mechanism. The biopsy probe mechanism includes an elongate sample receiving member having a longitudinal axis and a cutting cannula arranged coaxially with the sample receiving member. The elongate sample receiving member has a first echogenic feature. The cutting cannula has a second echogenic feature. The elongate sample receiving member and the cutting cannula are movable relative to one another by operation of the driver assembly between a first relative position and a second relative position. The first echogenic feature is in longitudinal alignment with the second echogenic feature when the elongate sample receiving member and the cutting cannula are in the first relative position to facilitate creation of a single composite echogenic reflection with respect to the first echogenic feature and the second echogenic feature. The first echogenic feature is out of longitudinal alignment with the second echogenic feature when the elongate sample receiving member and the cutting cannula are in the second relative position to facilitate creation of individual echogenic reflections with respect to the first echogenic feature and the second echogenic feature.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein.

Corresponding reference characters indicate corresponding parts throughout the several views. The exemplifications set out herein illustrate an exemplary embodiment of the invention, and such exemplifications are not to be construed as limiting the scope of the invention in any manner.

DETAILED DESCRIPTION OF THE INVENTION

Figure 1:
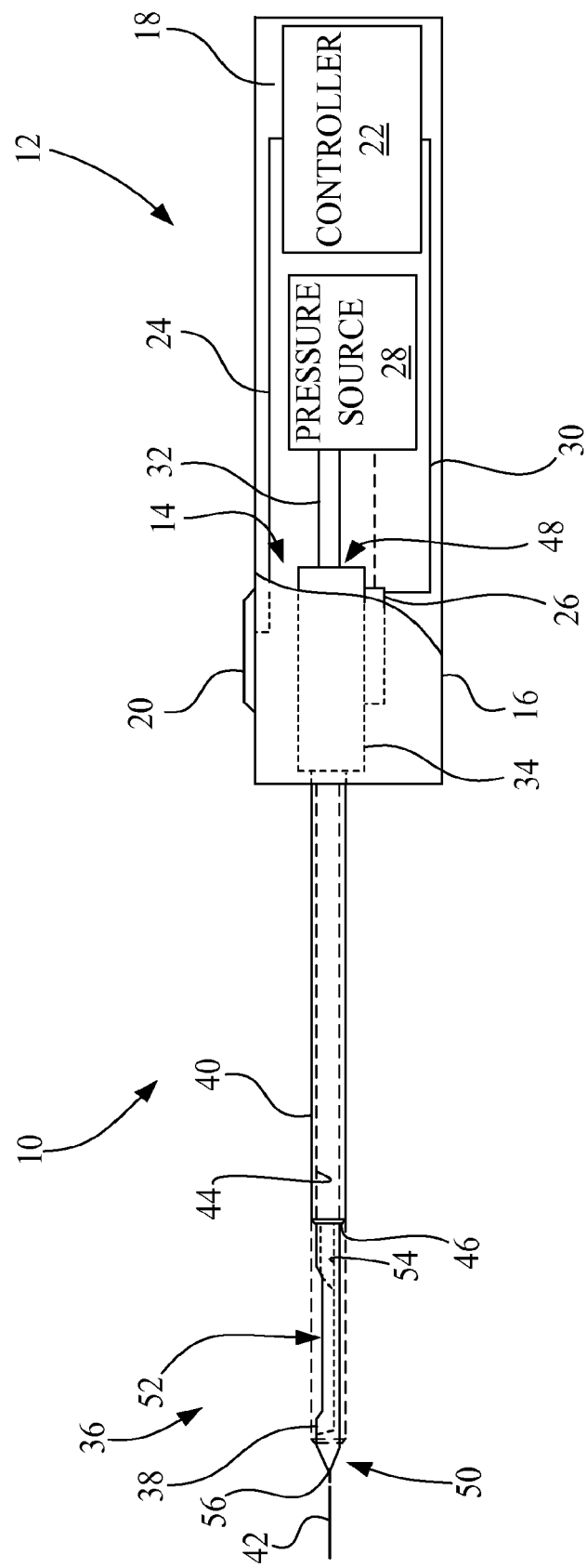
FIG. 1 is a side view of the biopsy apparatus of having a biopsy probe mechanism mounted to a biopsy driver assembly, and with a side portion broken away on the biopsy driver assembly to expose internal components which are schematically represented in part.

Referring now to the drawings, and more particularly to FIG. 1, there is shown a biopsy apparatus 10 configured in accordance with an embodiment of the invention Referring to FIG. 1, biopsy apparatus 10 includes a driver assembly 12 and a biopsy probe mechanism 14. Driver assembly 12 is configured to provide operative control over biopsy probe mechanism 14. Driver assembly 12 includes a housing 16 configured, e.g., ergonomically designed, to be grasped by a user, e.g., a physician. Housing 16 defines a compartment 18 into which biopsy probe mechanism 14 is at least partially positioned when biopsy probe mechanism 14 is attached to driver assembly 12, with biopsy probe mechanism 14 being drivably coupled to driver assembly 12.

Driver assembly 12 further includes a user interface 20 located to be externally accessible to the user with respect to housing 16 for receiving operation commands from the user, e.g., through one or more pushbuttons, and may also include a display, e.g., one or more lights or an LCD (liquid crystal display), to display information to the user. A controller 22 is communicatively coupled user interface 20 via a communication link 24, such as for example, wire cabling, printed circuits, etc. Controller 22 may include, for example, a microprocessor and associated memory (not shown) for executing program instructions to perform functions associated with the harvesting of biopsy tissue samples during a biopsy procedure.

There is contained within housing 16 an electromechanical drive 26 and a pressure source 28. Electromechanical drive 26 is connected in electrical communication with controller 22 via a communication link 30, such as for example, wire cabling, printed circuits, etc. Electromechanical drive 26 is further drivably coupled (illustrated by dashed lines) to the biopsy probe mechanism 14 and to the pressure source 28 to selectively and operatively control biopsy probe mechanism 14 and pressure source 28. Electromechanical drive 26 may include, for example, one or more of a linear drive that converts rotational motion to linear motion (e.g., a worm gear arrangement, rack and pinion arrangement, solenoid-slide arrangement, etc.) and a rotational drive that may include one or more of a gear, gear train, belt/pulley arrangement, etc., for effecting operation of biopsy probe mechanism 14 and/or pressure source 28.

Pressure source 28 may be, for example, a peristaltic pump, a diaphragm pump, syringe-type pump, etc. Pressure source 28 may be permanently integrated into driver assembly 12, or alternatively may be permanently integrated as a part of the biopsy probe mechanism 14. In either case, pressure source 28 is coupled in fluid communication with biopsy probe mechanism 14, e.g., via conduit 32, and is configured to generate negative pressure (vacuum), and in some embodiments may also generate positive pressure.

Biopsy probe mechanism 14 is generally intended to be disposable as a unit and intended for use on a single patient. Biopsy probe mechanism 14 includes a frame 34 to which is attached a biopsy probe 36. Biopsy probe 36 includes an elongate sample receiving member 38 and a cutting cannula 40. Sample receiving member 38 and a cutting cannula 40 are mounted as a coaxial unit to frame 34. In the present embodiment, for example, sample receiving member 38 is fixedly mounted to frame 34, with cutting cannula 40 and sample receiving member 38 being movably coupled together, and thus cutting cannula 40 is movably mounted to frame 34.

Each of sample receiving member 38 and cutting cannula 40 may be made, for example, from a metal, such as stainless steel, titanium, or a nickel alloy. Frame 34 may be made, for example, from plastic.

Sample receiving member 38 and a cutting cannula 40 are arranged coaxially with respect to a longitudinal axis 42, and are movable relative to one another along longitudinal axis 42. In the present embodiment illustrated in FIG. 1, for example, cutting cannula 40 is formed as a cylindrical tube having a lumen 44 and a distal cutting edge 46. Sample receiving member 38 is positioned in lumen 44 of cutting cannula 40, such that sample receiving member 38 slides longitudinally within cutting cannula 40.

In the present embodiment, sample receiving member 38 may be formed, for example, as an elongate cylindrical tube having a proximal end 48, a distal end 50, a sample receiving notch 52, and a lumen 54 (shown by dashed lines). In the present embodiment, a piercing tip 56 is located at distal end 50. Longitudinal axis 42 extends through proximal end 48 and distal end 50 in a central portion of lumen 54.

Those skilled in the art will recognize that as an alternative to the configuration of the exemplary embodiment of FIG. 1 having sample receiving member 38 slidably positioned within the lumen of cutting cannula 40, alternatively, cutting cannula 40 may be sized to be slidably positioned within the tube of sample receiving member 38.

Sample receiving notch 52 is formed in sample receiving member 38, such as for example, by machining a portion of a side wall 58 (see FIG. 2B) of sample receiving member 38 such that sample receiving notch 52 extends into an interior 60 of sample receiving member 38. Sample receiving notch 52 is located proximal to the distal end 50 of sample receiving member 38. Sample receiving notch 52 is configured to receive the tissue to be biopsied, and to collect the tissue sample harvested from the tissue, during a biopsy procedure. Sample receiving notch 52 also may be sometimes referred to as a sample chamber. Sample receiving notch 52 in sample receiving member 38 is coupled in fluid communication with pressure source 28 via conduit 32. It is to be understood, however, that some designs of biopsy apparatus 10 may not utilize a pressure source.

Figure 2A:
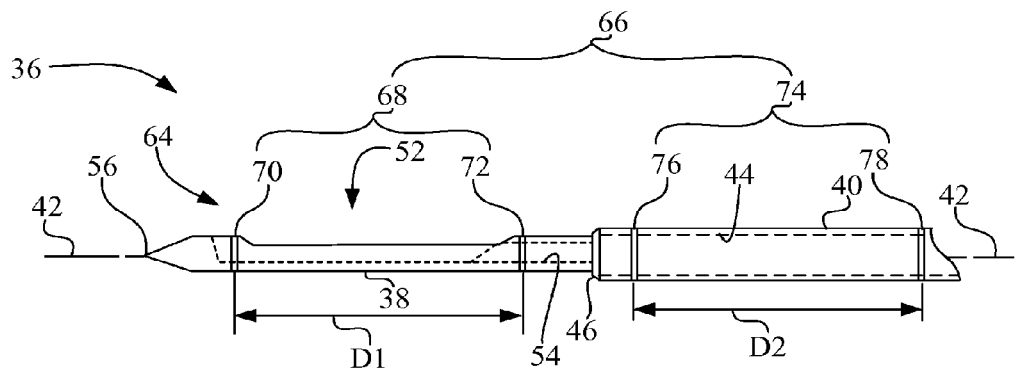
FIG. 2A is a side view of a portion of the biopsy probe of the biopsy apparatus of FIG. 1, with the sample receiving notch open, and having a plurality of echogenic features.
Figure 2B:
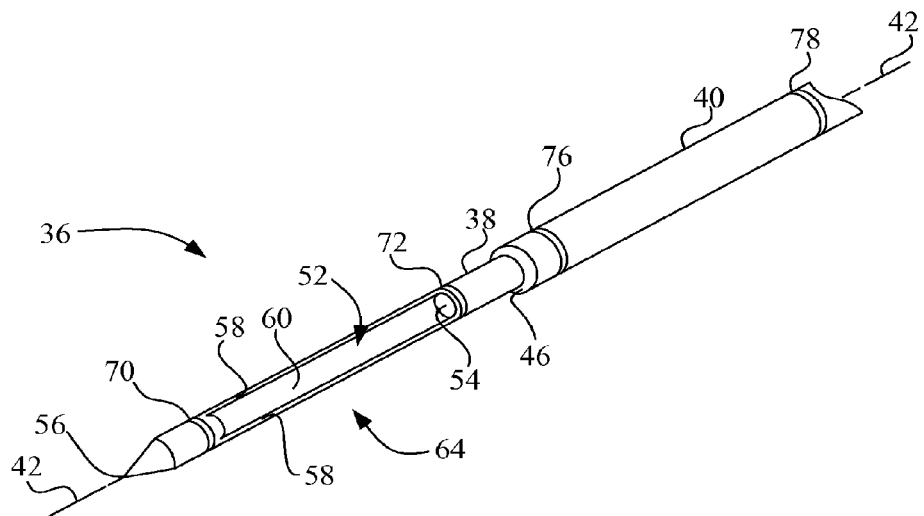
FIG. 2B is a perspective view of the portion of the biopsy probe of FIG. 2A.
Figure 3:
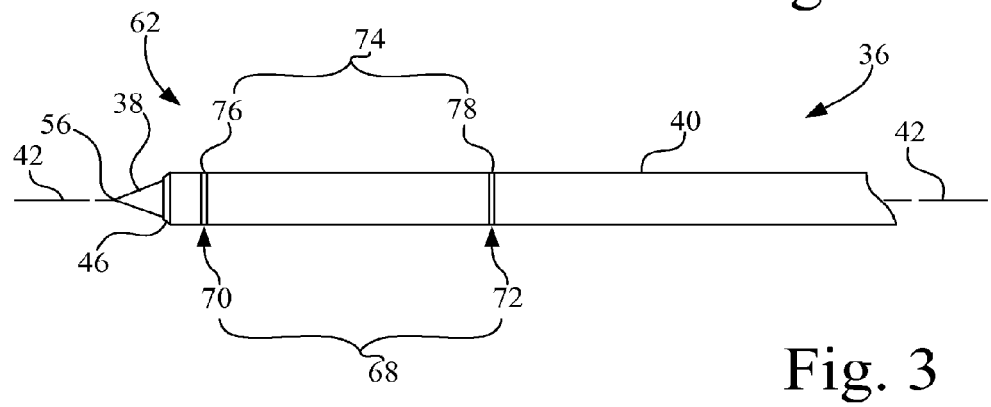
FIG. 3 is a side view of a portion of the biopsy probe of the biopsy apparatus of FIG. 1, with the sample receiving notch closed.

Referring also to FIGS. 2A, 2B and 3, sample receiving member 38 and cutting cannula 40 are movable relative to one another along longitudinal axis 42 between a first relative position 62 (FIG. 3) wherein sample receiving notch 52 is closed by cutting cannula and a second relative position 64 (FIGS. 2A and 2B) wherein sample receiving notch 52 is open. The term "closed" means that a pathway does not exist from a region outside biopsy probe 36 to the interior 60 of sample receiving member 38 via sample receiving notch 52. The term "open" means an unobstructed pathway exists from a region outside biopsy probe 36 to the interior 60 of sample receiving member 38 via sample receiving notch 52.

Referring now to FIGS. 2A and 2B, biopsy probe 36 of biopsy probe mechanism 14 includes a plurality of echogenic features 66. In the present exemplary embodiment, the plurality of echogenic features 66 includes a first set of echogenic features 68 that includes two individual echogenic features 70, 72 and a second set of echogenic features 74 that includes two individual echogenic features 76, 78.

In the present exemplary embodiment, each echogenic feature 70, 72, 76, 78 of the plurality of echogenic features 66 is representative of at least one circumferential band, i.e., one circumferential band, or alternatively multiple circumferential bands closely spaced, that forms a single echogenic reflection during ultrasonic imaging. It is contemplated that the circumferential echogenic band may extend partially, or completely, around the circumference of the respective object. Also, each circumferential echogenic band may be circumferentially continuous, circumferentially segmented, or of irregular shape. Each echogenic feature 70, 72, 76, 78 may be formed, for example, as at least one of a roughened surface, an embedded material, a machined pattern and a particulate coating, for providing a distinct contrasting echogenic reflection from that of the surrounding areas during ultrasound imaging.

In the embodiment depicted in FIGS. 2A, 2B and 3, the two echogenic features 70, 72 of the first set of echogenic features 68 are longitudinally spaced by a distance D1 and established on sample receiving member 38. Sample receiving notch 52 is located between the two longitudinally spaced echogenic features 70, 72. In other words, one of the echogenic features, e.g., echogenic feature 70, is located distal to sample receiving notch 52 and the other of the echogenic features, e.g., echogenic feature 72, is located proximal to sample receiving notch 52.

The echogenic features 76, 78 of the second set of echogenic features 74 are longitudinally spaced by a distance D2 and established on cutting cannula 40. In the present embodiment, the spacing distance D1 of the two longitudinally spaced echogenic features 70, 72 of the first set of echogenic features 68 is the same as the spacing distance D2 of the two longitudinally spaced echogenic features 76, 78 of the second set of echogenic features 74.

Thus, when elongate sample receiving member 38 and cutting cannula 40 are in the relative position 64, as depicted in FIGS. 2A and 2B, the first set of echogenic features 68 is out of longitudinal alignment with the second set of echogenic features 74, such that both of the first set of echogenic features 68 and the second set of echogenic features 74 is ultrasonically visible, i.e., the four echogenic features 70, 72, 76, 78 create four corresponding echogenic reflections that are ultrasonically visible.

Conversely, when elongate sample receiving member 38 and cutting cannula 40 are in the relative position 62, as depicted in FIG. 3, the first set of echogenic features 68 is in longitudinal alignment with the second set of echogenic features 74 such that only one set of echogenic features (i.e., two echogenic reflections) is ultrasonically visible, i.e., two echogenic bands are ultrasonically visible. Thus, when biopsy probe 36 is positioned in the tissue of a patient, the physician viewing the ultrasound image can easily discern whether sample receiving notch 52 of sample receiving member 38 is positioned adjacent a lesion of interest, and whether sample receiving notch 52 is open or closed, regardless of whether or not sample receiving notch 52 has been extended distally beyond distal cutting edge 46 of cutting cannula 40.

Described in another way, when elongate sample receiving member 38 and cutting cannula 40 are in the relative position 64, as depicted in FIGS. 2A and 2B, echogenic feature 70 of sample receiving member 38 is out of longitudinal alignment with echogenic feature 76 of cutting cannula 40, and echogenic feature 72 of sample receiving member 38 is out of longitudinal alignment with echogenic feature 78 of cutting cannula 40, and thus four echogenic reflections, e.g., bands, are ultrasonically visible.

Conversely, when elongate sample receiving member 38 and cutting cannula 40 are in the relative position 62, as depicted in FIG. 3, echogenic feature 70 of sample receiving member 38 is in longitudinal alignment with echogenic feature 76 of cutting cannula 40, and echogenic feature 72 of sample receiving member 38 is in longitudinal alignment with echogenic feature 78 of cutting cannula 40, and thus two echogenic reflections are ultrasonically visible. Note that although in FIG. 3 echogenic features 70, 72 are covered over by cutting cannula 40, echogenic features 70, 72 are still ultrasonically visible through cutting cannula 40, and thus the relative positioning of sample receiving member 38 and cutting cannula 40 in first relative position 62 (FIG. 3) is confirmed since only two echogenic bands are ultrasonically visible due to echogenic feature alignment.

Thus, one useful aspect of the configuration described above is that with respect to sample receiving member 38 the echogenic features 70, 72 delineate the extent of sample receiving notch 52, and thus the physician will know through the ultrasonic image the precise location of the portion of the sample receiving member 38 that corresponds to sample receiving notch 52, regardless of whether sample receiving notch 52 is open or closed.

Another useful aspect is that of confirmation of the relative positions of sample receiving member 38 and cutting cannula 40 of biopsy probe 36 during opening or closing of sample receiving notch 52, such as in the event of interference. For example, since the echogenic features 70, 72 of sample receiving member 38 are ultrasonically visible even when covered by cutting cannula 40, it is possible to track the progression of the opening and closing of sample receiving notch 52 of sample receiving member 38, as further described below.

With reference also the FIGS. 4-7, for example, assume sample receiving notch 52 is closed (the relative position shown in FIG. 3) and biopsy probe 36 is inserted, either manually or by a piercing shot, into the tissue TS of a patient for purposes of obtaining a biopsy, and the positioning of biopsy probe 36 is being observed using an ultrasound device 80. In preparation for insertion of biopsy probe 36 of biopsy probe mechanism 14 into a patient, for example, cutting cannula 40 was controlled by controller 22 and electromechanical drive 26 to translate linearly along longitudinal axis 42 to cover sample receiving notch 52 (shown in phantom lines in FIG. 1) of sample receiving member 38. In operation, a user may use piercing tip 56 of biopsy probe 36 to establish an access pathway through tissue TS to a biopsy site, either by manual insertion or by a piercing shot.

Figure 4:
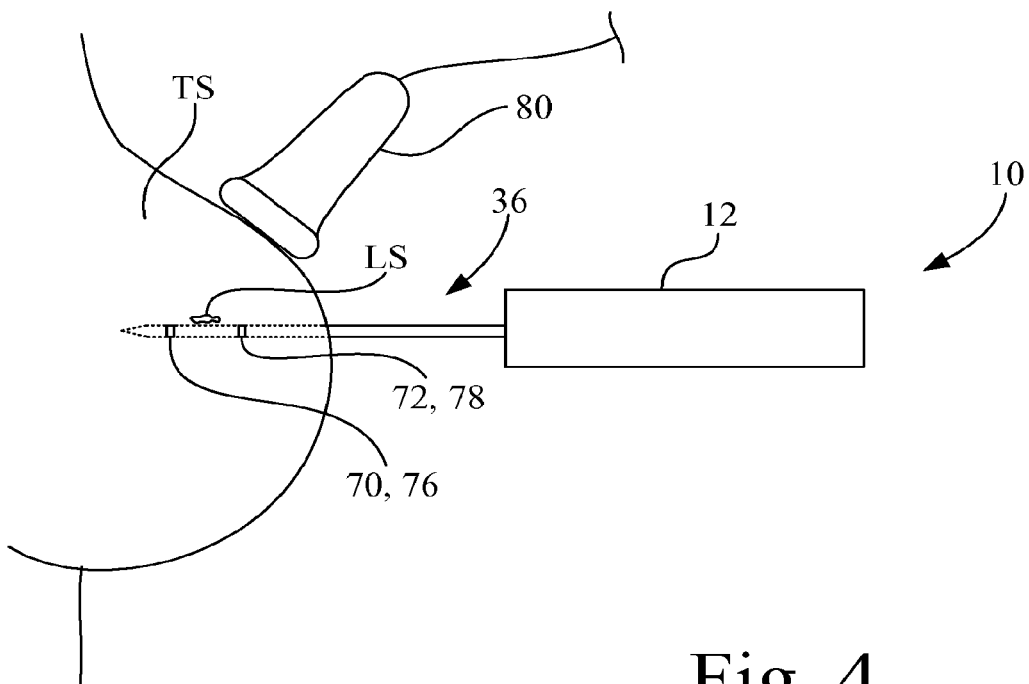
FIG. 4 is a diagrammatic illustration of the use of the biopsy apparatus of FIG. 1 in a biopsy procedure using ultrasound imaging.

Initially, as diagrammatically depicted in FIG. 4, the physician will observe two echogenic reflections, e.g., bands, as a single composite echogenic reflection 70, 76 associated with echogenic feature 70 and echogenic feature 76, and as a second single composite echogenic reflection 72, 78 associated with echogenic feature 72 and echogenic feature 78, due to echogenic feature alignment at the relative position 62 shown in FIG. 3. The two composite echogenic reflections 70, 76 and 72, 78 may be used to precisely locate sample receiving notch 52 relative to the location of the lesion LS of interest.

Figure 5:
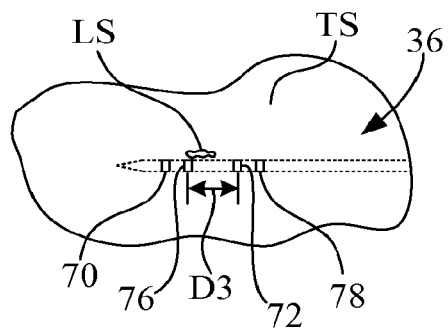
FIG. 5 is a diagrammatic illustration of an initial stage of the opening of the sample receiving notch visualized by observation of the positions of the echogenic features using ultrasound imaging.
Figure 6:
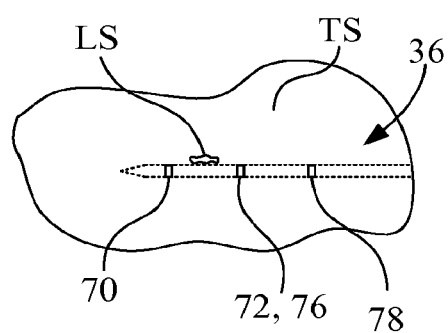
FIG. 6 is a diagrammatic illustration of an intermediate stage of the opening of the sample receiving notch visualized by observation of the positions of the echogenic features using ultrasound imaging.
Figure 7:
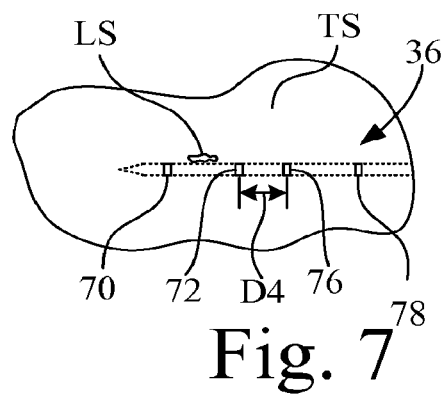
FIG. 7 is a diagrammatic illustration of a final stage of the opening of the sample receiving notch visualized by observation of the positions of the echogenic features using ultrasound imaging.

Thereafter, cutting cannula 40 is then controlled by controller 22 and electromechanical drive 26 to translate linearly along longitudinal axis 42 to expose sample receiving notch 52. As diagrammatically depicted in FIG. 5, during the opening of sample receiving notch 52, e.g., by retraction of cutting cannula 40 with respect to sample receiving member 38, the physician will observe four echogenic reflections, e.g., bands, corresponding to echogenic features 70, 72, 76, 78. As illustrated in FIG. 5, echogenic feature 76 of cutting cannula 40 is proximal to echogenic feature 70 of sample receiving notch 52 and the distance D3 between echogenic feature 76 of cutting cannula 40 and echogenic feature 72 of sample receiving member 38 decreases until three echogenic reflections are observed as illustrated in FIG. 6. The three echogenic reflections are observed when echogenic feature 76 of cutting cannula 40 is in longitudinal alignment with echogenic feature 72 of sample receiving member 38 to generate a composite echogenic reflection 72, 76, and with individual echogenic features 70 and 78 also being ultrasonically visible.

Immediately thereafter, with further relative movement of cutting cannula 40 with respect to sample receiving member 38, four echogenic reflections are again observed with echogenic feature 76 of cutting cannula 40 now being proximal to echogenic feature 72 of sample receiving member 38, and with the distance D4 between echogenic feature 72 of sample receiving member 38 and echogenic feature 76 of cutting cannula 40 increasing until sample receiving notch 52 is open and the relative position 64 is reached, as depicted in FIGS. 2A and 2B.

Thereafter, controller 22 initiates pressure source 28 to establish a vacuum in sample receiving notch 52, thereby drawing all or a portion of lesion LS into sample receiving notch 52. Cutting cannula 40 is then controlled by controller 22 and electromechanical drive 26 to translate linearly along longitudinal axis 42 to close, e.g., cover, sample receiving notch 52 and sever the tissue in sample receiving notch 52, until relative position 62 of sample receiving member 38 and cutting cannula 40 is achieved, as depicted in FIG. 3. Also, cutting cannula 40 may be controlled to rotate or oscillate with, or independent from, any linear advancement of cutting cannula 40. During the cutting process, i.e., during the closure of sample receiving notch 52, the positions of echogenic features 70, 72, 76 and 78 will be the reverse of the ultrasonic observations described above with respect to the opening of sample receiving notch 52.

The tissue sample having been collected, biopsy probe 36 may be withdrawn from the patient.

While this invention has been described with respect to an embodiment, the present invention can be further modified within the spirit and scope of this disclosure. For example, in some applications it may be desirable to have a single echogenic feature on each of the sample receiving member and the cutting cannula. Also, for example, in some applications it may be desirable to have more that two echogenic features on each of the sample receiving member and the cutting cannula. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A biopsy probe mechanism, comprising:
    an elongate sample receiving member having a longitudinal axis and having a sample receiving notch;
    a cutting cannula arranged coaxially with the elongate sample receiving member, the elongate sample receiving member and the cutting cannula being movable relative to one another along the longitudinal axis; and
    a plurality of echogenic features including a first echogenic feature established on the elongate sample receiving member and a second echogenic feature established on the cutting cannula, and the elongate sample receiving member and the cutting cannula configured to have a first position in which the first echogenic feature is in longitudinal alignment with the second echogenic feature, and configured such that when the elongate sample receiving member and the cutting cannula are moved relative to one another from the first position, the first echogenic feature and the second echogenic feature are out of longitudinal alignment,
    wherein the elongate sample receiving member has a proximal end and a distal end, the sample receiving notch being located proximal to the distal end, the plurality of echogenic features including a third echogenic feature established on the elongate sample receiving member, with one of the first echogenic feature and the third echogenic feature being located distal to the sample receiving notch and the other of the first echogenic feature and the third echogenic feature being located proximal to the sample receiving notch,
    and
    wherein the plurality of echogenic features includes a fourth echogenic feature established on the cutting cannula at a location spaced apart from the second echogenic feature,
    the third echogenic feature being in longitudinal alignment with the fourth echogenic feature when the elongate sample receiving member and the cutting cannula are in the first position, and
    the third echogenic feature being out of longitudinal alignment with the fourth echogenic feature when the elongate sample receiving member and the cutting cannula are not in the first position.

2. The biopsy probe mechanism of claim 1, wherein the sample receiving notch in the elongate sample receiving member is closed by the cutting cannula when the first echogenic feature and the second echogenic feature are in longitudinal alignment, and configured such that when the sample receiving notch is opened the first echogenic feature and the second echogenic feature are out of longitudinal alignment.

3. The biopsy probe mechanism of claim 1, wherein each echogenic feature of the plurality of echogenic features includes at least one circumferential echogenic band.

4. The biopsy probe mechanism of claim 1, wherein each echogenic feature of the plurality of echogenic features is formed as at least one of a roughened surface, an embedded material, a machined pattern and a particulate coating for providing a distinct echogenic reflection from surrounding areas during ultrasound imaging.

5. The biopsy probe mechanism of claim 1, wherein the biopsy probe mechanism is configured as a disposable unit.

6. The biopsy probe mechanism of claim 1, wherein the biopsy probe mechanism is integrated into a biopsy apparatus having a driver for driving the biopsy probe mechanism.

7. A biopsy apparatus for use in conjunction with an ultrasound device, comprising:
 a driver assembly; and
 a biopsy probe mechanism coupled to the driver assembly, the driver assembly being configured to provide operative control over the biopsy probe mechanism, the biopsy probe mechanism including an elongate sample receiving member having a longitudinal axis and a cutting cannula arranged coaxially with the elongate sample receiving member, and including a first echogenic feature established on the elongate sample receiving member and a second echogenic feature established on the cutting cannula, and
 the elongate sample receiving member and the cutting cannula configured to have a first position in which the first echogenic feature is in longitudinal alignment with the second echogenic feature to facilitate creation of a single echogenic reflection, and configured such that when the elongate sample receiving member and the cutting cannula are moved relative to one another from the first position, the first echogenic feature and the second echogenic feature are out of longitudinal alignment to facilitate creation of separate individual echogenic reflections with respect to the first echogenic feature and the second echogenic feature,
 wherein the elongate sample receiving member has a proximal end and a distal end, and the elongate sample receiving member having a sample receiving notch being located proximal to the distal end, the elongate sample receiving member having a third echogenic feature, with one of the first echogenic feature and the third echogenic feature being located distal to the sample receiving notch and the other of the first echogenic feature and the third echogenic feature being located proximal to the sample receiving notch, and
 wherein the cutting cannula has a fourth echogenic feature spaced apart from the second echogenic feature, and wherein the elongate sample receiving member and the cutting cannula are configured such that:
 when the elongate sample receiving member and the cutting cannula are in the first position the third echogenic feature is in longitudinal alignment with the fourth echogenic feature to facilitate creation of a single echogenic reflection, and
 when the elongate sample receiving member and the cutting cannula are not in the first position the third echogenic feature is out of longitudinal alignment with the fourth echogenic feature to facilitate creation of separate individual echogenic reflections with respect to the third echogenic feature and the fourth echogenic feature.

8. The biopsy apparatus of claim 7, wherein each echogenic feature includes at least one circumferential echogenic band.

9. The biopsy apparatus of claim 8, wherein each circumferential echogenic band is formed as at least one of a roughened surface, an embedded material, a machined pattern and a particulate coating for providing a distinct echogenic reflection from surrounding areas during ultrasound imaging.

10. The biopsy apparatus of claim 7, wherein the elongate sample receiving member has a sample receiving notch that is closed by the cutting cannula when in the first position.

* * * * *